United States Patent [19]
Mitoh et al.

[11] Patent Number: 5,851,670
[45] Date of Patent: Dec. 22, 1998

[54] IN VIVO-SOLUBLE COMPOSITE PARTICLES COMPRISING CALCIUM PHOSPHATE

[75] Inventors: Ayumi Mitoh; Tetsuro Ogawa, both of Tokyo, Japan

[73] Assignee: Asahi Kogaku Kogyo Kabushiki Kaisha, Tokyo, Japan

[21] Appl. No.: 790,984

[22] Filed: Jan. 29, 1997

[30] Foreign Application Priority Data

Jan. 29, 1996 [JP] Japan ..................................... 8-013385

[51] Int. Cl.⁶ ............................. B32B 5/16; A01N 59/26; A61K 9/16
[52] U.S. Cl. ........................... 428/403; 424/490; 424/492; 424/496; 424/602; 428/407; 428/702; 428/704
[58] Field of Search ..................................... 428/403, 407, 428/702, 704; 424/490, 492, 496, 602, 603

[56] References Cited

U.S. PATENT DOCUMENTS

| | | | |
|---|---|---|---|
| 4,781,904 | 11/1988 | Tagaya et al. ........................... | 423/308 |
| 4,952,323 | 8/1990 | Nakabayashi et al. .................. | 210/691 |
| 5,030,391 | 7/1991 | Sumita et al. ............................... | 264/5 |
| 5,055,307 | 10/1991 | Tsuru et al. .............................. | 424/493 |
| 5,085,781 | 2/1992 | Tsuru et al. .............................. | 210/692 |
| 5,098,842 | 3/1992 | Nakajima et al. ....................... | 435/287 |
| 5,540,995 | 7/1996 | Kitano et al. ............................ | 428/407 |

FOREIGN PATENT DOCUMENTS

| | | |
|---|---|---|
| 0420053 | 4/1991 | European Pat. Off. . |
| 1-51266 | 11/1989 | Japan . |
| 2200628 | 8/1990 | Japan . |
| 2282548 | 4/1995 | United Kingdom . |
| 2293009 | 3/1996 | United Kingdom . |

OTHER PUBLICATIONS

Derwent WPI Acc No. 89–088903/12 of JP 1038658, published Feb. 8, 1989,
Derwent WPI Acc No. 89–088902/12 of JP 1038657, published Feb. 8, 1989.

*Primary Examiner*—H. Thi Le
*Attorney, Agent, or Firm*—Greenblum & Bernstein, P.L.C.

[57] ABSTRACT

In vivo-soluble composite particles involving a particle of a polymeric substance such as polylactic acid and the like soluble in a living body, having coated on a surface thereof, a calcium phosphate compound having a Ca/P ratio of about 1.0 to 2.0. The in vivo-soluble composite particles have a highly increased adsorptivity with regard to medicaments, antigens and others and also the in vivo-soluble composite particles can be dissolved or decomposed in the living body without producing a remainder in the body.

8 Claims, No Drawings

IN VIVO-SOLUBLE COMPOSITE PARTICLES COMPRISING CALCIUM PHOSPHATE

BACKGROUND OF THE INVENTION

1. Field of the Invention

The present invention relates to an in vivo-soluble composite particle, i.e., particles of composite material soluble in a living body or organism.

2. Description of the Related Art

One typical and well-known method for carrying out a drug delivery system in which a drug or medicament can be directly supplied to a desired area (focus) of a patient is through endermic catheterization. The catheterization can be utilized in the medical treatment of malignant tumors, such as cancer, by using medicaments. Even if the medicaments used generate strong side effects, since they are supplied exactly to only a targeted site of the patient, the side effects are not caused. For example, Japanese Examined Patent Publication (Kokoku) No. 1-51266 and Japanese Unexamined Patent Publication (Kokai) No. 2-200628, each teaches the use of a carcinostatic substance or agent adsorbed on particles of calcium phosphate compound for the purpose of treating tumors.

Using the drug delivery system, when the calcium phosphate particles with the adsorbed carcinostatic or other medicaments are applied to a predetermined site of a blood vessel, the adsorbed medicaments are gradually released from the particles in the blood vessel while retaining the functions and effects of the medicaments therein for a certain period of time. However, due to a high specific gravity thereof, there is a risk that the calcium phosphate particles may cause clogging or infarction of the blood vessel.

Alternatively, there is a well-known method of using a spongy gelatin having a medicament impregnated therein. However, this method suffers from the drawbacks that the gelatin carries an insufficient amount of medicament, and that an extended maintenance of the effects of the carried medicament can not be expected because of the rapid dissolution of the gelatin in the blood.

SUMMARY OF THE INVENTION

The object of the present invention is to provide an improved in vivo-soluble particle having a highly increased adsorptivity with regard to medicaments, antigens and others, which can be dissolved or decomposed in the living body or organism without producing an in vivo remainder in the organism.

According to the present invention, the above object can be accomplished by forming a core of the in vivo-soluble particle from a particle of a polymeric substance soluble in a living organism and coating a surface of the particle as a core with a calcium phosphate compound having a good adsorptivity.

Namely, the in vivo-soluble composite particle of the present invention is characterized by having a coating of calcium phosphate compound having a Ca/P ratio of about 1.0 to 2.0 applied on a surface of the particle of the in vivo-soluble polymeric substance.

The in vivo-soluble composite particle of the present invention, since its surface has a layer or coating of calcium phosphate compound having a high adsorptivity, can be used in a drug delivery system, thereby a medicament can be directly applied to a predetermined site of the focus, after the medicament has been adsorbed onto the calcium phosphate layer or coating. Upon the direct application of the medicament to the focus site, it becomes possible to retain a high concentration of the medicament around the focus site. Further, since the calcium phosphate compound is supplied in the form of fine particles on a surface portion of the composite particle, it can be gradually eaten with macrophages, thereby enabling the exposure of the underlying core, i.e., in vivo-soluble polymeric substance. Since it can be dissolved by a body fluid, the exposed core or polymeric substance is dissipated along with the calcium phosphate layer or coating, after the release of the medicament. Finally, no residue is produced in the living body.

Alternatively, according to the present invention, an antigen can be adsorbed in the in vivo-soluble composite particle of the present invention for the purpose of applying the antigen to a living organism such as a human body, thereby obtaining an increased antibody titer.

The present disclosure relates to subject matter contained in Japanese Patent Application No. 8-13385 (filed on Jan. 29, 1996) which is expressly incorporated herein by reference in its entirety.

DESCRIPTION OF THE PREFERRED EMBODIMENTS

In the in vivo-soluble composite particle of the present invention, the particle of the in vivo-soluble polymeric substance is used as a core of the composite particle. The polymeric substance used herein as the core is not restrictive, if it can be dissolved in a body fluid in a living organism, such as a human body. However, the polymeric substance should preferably be a physiologically acceptable substance. Typical examples of suitable polymeric substances include gelatin, polylactic acid, chitin, polyvinyl alcohol, polyacrylic acid, collagen and the like. The chitin used herein can be finally decomposed with an enzyme lysozyme in the living organism and thus becomes soluble in the organism. Note that the term "in vivo-soluble" used herein, is intended to include substances such as the above-mentioned chitin, namely, those capable of becoming soluble upon decomposition with an enzyme or other substances present in a living organism.

The in vivo-soluble composite particle of the present invention can be prepared by coating a surface of the particle of the in vivo-soluble polymeric substance with a calcium phosphate compound. Any conventional coating method may be used in the formation of the calcium phosphate coating, however, it is preferred to physically impinge particles of the calcium phosphate compound onto the particles of the in vivo-soluble polymeric substance, thereby producing a coating of the calcium phosphate compound over each particle of the polymeric substance along with penetration of at least a part of the calcium phosphate compound into pores of the particle of the polymeric substance.

Preferably, the particles of the in vivo-soluble polymeric substance used herein generally comprise particles having an average particle diameter of about 1 to 20 microns within a particle size distribution of $d_{75}/d_{25} \leq 2$ in which $d_{25}$ refers to a particle size determined when the cumulative undersize particle of the particles is approximately 25%, and $d_{75}$ refers to a particle size determined when the cumulative undersize particle of the particles is approximately 75%. "Undersize particle" means a particle having a diameter less than a given diameter. "Cumulative undersize particle" means the sum of undersize particles which have a diameter equal to or less than a given diameter. In the case of $d_{25}$, the "cumulative undersize particle" is about 25% of the whole sum of the particles. In the case of $d_{75}$, the "cumulative undersize particle" is about 75% of the whole sum of the particles. To illustrate these definitions by way of example, suppose that the number of particles is plotted versus the diameter of the particles so as to form a bell curve distribution. To determine $d_{25}$, the particles are cumulated from the smallest particle diameter until the sum becomes 25% of the whole sum of the particles. The diameter of the particles at the 25% point is equal to $d_{25}$. Also, the "cumulative undersize particle" is represented by the area under the bell curve from the smallest particle diameter to $d_{25}$. The average particle diameter of the polymeric particles of less than about 1 micron will cause a remarkable reduction of the penetration degree or depth of the calcium phosphate compound therein, and an average particle diameter of more than about 20 microns will cause a difficulty in the production of the composite particles having a highly increased density because of a varied and unstable density thereof.

Further, the particles of the in vivo-soluble polymeric substance preferably have a density of about 0.9 to 1.2 g/cm$^3$. When the resulting composite particles are intended to be used in a liquid, it is preferred that the polymeric particles have a density of about 0.9 g/cm$^3$ or more, since the composite particles should preferably have a density higher than the specific gravity of water. It is also preferred from the view point of the physical impingement process applied in the production of the composite particles and the practical use of the composite particles, that the polymeric particles have a density of not more than about 1.2 g/cm$^3$.

As mentioned above, in the in vivo-soluble composite particles of the present invention, it is preferred that the composite particles comprise an in vivo-soluble polymeric particle as a core and calcium phosphate compound coated over a surface of the core, wherein at least a part of the coated particles of the calcium phosphate compound is impregnated or penetrated into the polymeric particles.

The calcium phosphate compound used herein is not restricted, insofar as it shows a Ca/P ratio in the range of about 1.0 to 2.0, and accordingly it includes a wide variety of calcium phosphate compounds. For example, one or more of $Ca_{10}(PO_4)_6(OH)_2$, $Ca_{10}(PO_4)_6F_2$, $Ca_{10}(PO_4)_6Cl_2$, $Ca_3(PO_4)_2$, $Ca_2P_2O_7$, $Ca_4O(PO_4)_2$, and $CaHPO_4$ may be used as the calcium phosphate compound. Among these calcium phosphate compounds, the most preferred is a calcium phosphate compound which contains hydroxyapatite as a principal component thereof. Preferably, the hydroxyapatite used therein has a Ca/P ratio in the range of about 1.65 to 1.67. When fluoroapatite is used as the calcium phosphate compound, it is preferred that a content of fluorine in all the calcium phosphate compounds used is not more than about 5% by weight, since a fluorine content above about 5% by weight can exhibit an undesirable elution of fluorine from such compounds. These calcium phosphate compounds may be produced by using any conventional production methods including a wet process, a dry process and other processes.

The particles of the calcium phosphate compound can be produced using any conventional granulation method. For example, they can be produced by spray-drying a slurry of the calcium phosphate compound, followed by granulating and calcining the dried product to obtain the intended particles of the calcium phosphate compound. Preferably, sieve and other separation means may be used to selectively produce particles of the calcium phosphate compound having the predetermined range of the particle size depending on the intended use of the particles.

Preferably, the particles of the calcium phosphate compound used in the practice of the present invention have an apparent density of about 1.5 to 2.5 g/cm$^3$. An apparent density of less than about 1.5 g/cm$^3$ will reduce the density of the resulting composite particles to a level lower than the density of water. On the contrary, an apparent density of more than about 2.5 g/cm$^3$ will cause a remarkable reduction of the adsorptivity thereof. Note that the term "apparent density" used herein is intended to mean a hydrous apparent density of the particles of the calcium phosphate compound, i.e., a density of the calcium phosphate particles which can be applied to determine a Storkes diameter of the particles in accordance with a settling method in which water is used as a dispersing medium. The apparent density of the particles can be calculated from the following schema:

$$V\infty = g \cdot dp^2 (\rho_p - \rho)/18\mu$$

in which $V\infty$ represents a terminal settling velocity, g represents gravity, $\rho_p$ represents an apparent density of the particles, dp represents a particle size or diameter of the particles, $\rho$ represents a density of water, and $\mu$ represents a viscosity of water.

Further, the particles of the calcium phosphate compound are preferably porous particles. More preferably, the porous calcium phosphate particles comprise agglomerated and bonded primary particles having a specific surface area of not less than about 10 m$^2$/g and a pore size of about 500 to 1000 angstroms. A specific surface area of less than about 10 m$^2$/g should be avoided, because such a specific surface area does not ensure a satisfactory adsorptivity. In addition, in order to attain an introduction of the adsorbed proteins and other substances into the pores or cells of the particles, it is preferred that the porous particles contain pores or cells having the above-mentioned pore size of about 500 to 1000 angstroms.

The porous particles of the calcium phosphate compound can be produced using any conventional method. For example, they can be produced from starting particles which are crystalline particles of the calcium phosphate compound synthesized in a well-known wet process. A slurry of the starting particles as a suspension is directly spray-dried or subjected to other treatments to form secondary particles, or is spray-dried or treated according to other methods to form secondary particles, after the addition of an additive such as a viscosity modifier, particles of an organic compound capable of being dissipated upon heating or fibers to the slurry.

The resulting secondary particles are porous particles in themselves, and accordingly they may be used as a starting material in the production of the composite particles. Alternatively, if it is desired to obtain porous particles or granules of the calcium phosphate compound having a highly increased porosity, such porous granules can be produced by preparing a slurry of the secondary particles as a suspension again, and then molding the slurry in a wet process or in a dry process including an application of pressure to produce a block body of the calcium phosphate compound. In the preparation of the slurry, any organic compound which may be dissipated from the block body during the subsequent calcination process may be added to the slurry in order to assist the formation of the pores or cells in the resulting granules. However, such an addition of the organic compound is optional, and therefore it may be omitted, if not desired, since a pore size or diameter of the resulting porous granules can be controlled by changing the calcination temperature and other conditions. The obtained block body is then calcined at a temperature ranging from about 500° C. to 1300° C. A calcination temperature of less than about 500° C. is insufficient to complete thermal dissipation of the organic compound and calcination of the block body. If the calcination of the block body is carried out at an elevated temperature above about 1300° C., an excessively densified calcined body can be produced or an undesired decomposition of the calcium phosphate can be caused. The thus calcined block body is pulverized and then classified or sieved to obtain porous granules having a desired porosity. The pore size of the porous granules can be controlled by suitably varying a size of the crystalline particles of the calcium phosphate compound in the starting slurry used in the preparation of the secondary particles, a viscosity of the slurry, additives and others.

In the production of the in vivo-soluble composite particles of the present invention, the physical impingement of the particles of the calcium phosphate compound against the particles of the in vivo-soluble polymeric substance includes a dry impingement process in which commercially available hybridization systems, such as Nara hybridization system NHS-1 commercially available from Kabushikikaisha Nara Kikai Seisakusho or Hi-X200 commercially available from Nissin Engineering Co. Ltd., are utilized. Generally, utilizing these hybridization systems, the particles of the calcium phosphate compound and the particles of the in vivo-soluble polymeric substance can be blended in a weight ratio of the calcium phosphate particles to the polymeric particles of about 0.05 to 0.50, under controlled temperature conditions so that the temperature of the system is not more than the softening temperature of the polymeric substance used, i.e., typically, 80° C. or less.

It is preferred that the particles of the calcium phosphate compound to be physically impinged against the particles of the in vivo-soluble polymeric substance have an average particle size of about 100 microns or less. Since the calcium phosphate particles are pulverized upon physical impingement, they may have a significantly large particle size in comparison with the polymeric particles, however, it should be noted that when the average particle size of the calcium phosphate particles is above about 100 microns, the velocity of the particles can be reduced during the impingement, and thus the calcium phosphate particles can not be satisfactorily pulverized, and that even if the calcium phosphate particles can be pulverized, the pulverized particles can not be satisfactorily penetrated into the polymeric particles.

The operation of the hybridization and other apparatuses used are preferably so controlled that during physical impingement of the calcium phosphate particles having an average particle size of about 100 microns or less against the in vivo-soluble polymeric particles, the calcium phosphate particles are penetrated into the polymeric particles, after pulverization thereof to a particle size of about 7 microns or less, at which size the calcium phosphates compound can be eaten by macrophages and the like in a living body.

In addition, an average particle size of the calcium phosphate particles penetrated into the polymeric particles upon the impingement is preferably in the range of about one fifth (⅕) or less, more preferably about one tenth (1/10) or less of that of the polymeric particles as the core. When the average particle size of the calcium phosphate particles used is above one fifth (⅕) of the average particle size of the core particles, there arises a tendency that a separating or releasing stability of the calcium phosphate compound may remarkably deteriorate.

In the above-mentioned physical impingement process, it is not required that the calcium phosphate particles are deeply penetrated such that they penetrate into at a central portion of the polymeric particles. Namely, it is sufficient in the practice of the present invention that the calcium phosphate particles are partly introduced and penetrated into the polymeric particles. When a part of the calcium phosphate particles is penetrated into the polymeric particles, the polymeric particles can fixedly receive the penetrated calcium phosphate particles, since they generally have a good elasticity and thus they can surround the penetrated calcium phosphate particles with an adequate holding pressure.

It is preferred that a layer or coating of the calcium phosphate compound having a thickness of about 0.1 to 5.0 microns is formed on a surface of the polymeric particles upon the physical impingement process. A layer thickness of less than about 0.1 micron results in an insufficient adsorptivity, while a layer thickness of more than about 5.0 microns does not cause an increase of the adsorptivity corresponding to such an increase in the layer thickness.

As a result, according to the present invention, the in vivo-soluble composite particles which have an average particle diameter of about 1.2 to 30.0 microns within a particle size distribution of $d_{75}/d_{25} \leq 2$, a density of about 1.05 to 1.35 g/cm$^3$ and a pore size of about 500 to 1000 angstroms, and in which a layer of the coated calcium phosphate compound has a thickness of about 0.1 to 5.0 microns, can be obtained. Further, using the present in vivo-soluble composite particles, it becomes possible to attain an adsorption level of the proteins in an amount of about 0.2 to 4.0 mg of lysozyme per gram.

The in vivo-soluble composite particles according to the present invention may be colored or dyed, if desired. Such colored composite particles may be produced, for example, by using previously colored particles of the in vivo-soluble polymeric substance in the production of the composite particles or dyeing the composite particles with any desirable dye, pigment or other coloring material after production thereof. The thus obtained colored composite particles can be advantageously utilized in order to distinguishably indicate the type or amount of the medicaments or others which will be adsorbed on the composite particles in the subsequent process.

Since they have a coating or layer of the finely divided calcium phosphate compound particles on a surface thereof, the present in vivo-soluble composite particles can exhibit a notably increased adsorptivity and therefore can be utilized in a drug delivery system for the purpose of selectively supplying a medicament to a predetermined site of the focus after adsorption of the medicament on the composite particles or can be utilized as an adjuvant after adsorption of an antigen on the composite particles.

The present invention will be further described with reference to working examples thereof. Note, however, that the present invention should not be restricted to these examples.

EXAMPLE 1

50 g of beads of poly-L-lactic acid (hereinafter, simply referred to as P-L-LA) having an average particle size of 5 microns and an apparent density of 1.07 g/cm$^3$ and 5.0 g of particles of hydroxyapatite having a Ca/P ratio of 1.67, an average particle size of 20 microns, a specific surface area of 24 m$^2$/g, a bulk density of 2.2 g/cm$^3$ and a pore size of 800 angstroms, were blended at 36 to 64° C. for 5 minutes on a Nara Kikai Hybridization System NHS-1 (commercially available from Nara Kikai Seisakusho; rated power: 5.5 kw and rated current: 23 A) at a rotation speed of 8000 rpm. A surface of the P-L-LA beads was thus coated with the hydroxyapatite. The resulting composite particles had an average particle diameter of 5.4 microns, a density of 1.05 to 1.15 g/$cm^3$ and a pore size of 800 angstroms, and an average thickness of the coated hydroxyapatite was 0.75 microns.

The composite particles produced in the above step and an egg-white lysozyme were mixed in a buffer solution of phosphate having a pH of 7.2. The egg-white lysozyme was adsorbed on the composite particles. After the adsorption step, the composite particles were washed with a buffer solution of phosphate having a pH of 7.2 to remove non-adsorbed lysozyme therefrom. After preparation of the composite particles in a level of 0.5 mg/mL, the preparation was administered to an abdominal cavity of a female ddy mouse of 4 weeks of age. The phrase "ddy mouse" means from a lineage of mice grown for general experiments. The "ddy mouse" is especially bred without mixing other lineages for more than 5 years, i.e., purebred. After one week, it was found that an antibody titer with regard to the lysozyme increased notably.

EXAMPLE 2

50 g of beads of chitin particles having an average particle size of 7 microns and 7.5 g of particles of hydroxyapatite having a Ca/P ratio of 1.67, an average particle size of 5 microns, a specific surface area of 45 $m^2$/g, a bulk density of 1.8 g/$cm^3$ and a pore size of 600 angstroms, were blended at 36° to 47° C. for 5 minutes on a Nara Kikai Hybridization System NHS-1 (commercially available from Nara Kikai Seisakusho; rated power: 5.5 kw and rated current: 23 A) at a rotation speed of 8000 rpm. A surface of the chitin beads was thus coated with the hydroxyapatite. The resulting composite particles had an average particle diameter of 5.8 microns and pore size of 600 angstroms, and a thickness of the coated hydroxyapatite was 0.8 micron.

The composite particles produced in the above step and an antigen of A-type influenza virus were mixed in a buffer solution of phosphate having a pH of 7.2. The influenza virus antigen was adsorbed on the composite particles. After the adsorption step, the composite particles were washed with a buffer solution of phosphate having a pH of 7.2 to remove non-adsorbed antigen therefrom. After preparation of the composite particles in a level of 0.5 mg/mL, the preparation was administered to an abdominal cavity of a female ddy mouse of 4 weeks of age. After one week, it was found that an antibody titer with regard to the A-type influenza increased notably.

What is claimed is:

1. In vivo-soluble composite particles which comprise a particle of a polymeric substance soluble in a living organism, having a calcium phosphate compound having a Ca/P ratio of about 1.0 to 2.0 coated on a surface thereof.

2. In vivo-soluble composite particles according to claim 1 in which said polymeric substance is selected from the group consisting of gelatin, polylactic acid, chitin, polyvinyl alcohol, polyacrylic acid, and collagen.

3. In vivo-soluble composite particles according to claim 1 in which said particle of said polymeric substance contains at least a part of said calcium phosphate compound penetrated therein.

4. In vivo-soluble composite particles according to claim 1 in which said particle of said polymeric substance comprises particles having an average particle diameter of about 1 to 20 microns within a particle size distribution of $d_{75}/d_{25} \leqq 2$.

5. In vivo-soluble composite particles according to claim 1 which have an average particle diameter of about 1.2 to 30.0 microns within a particle size distribution of $d_{75}/d_{25} \leqq 2$, a density of about 1.05 to 1.35 g/$cm^3$ and a pore size of about 500 to 1000 angstroms, and in which a layer of said coated calcium phosphate compound has a thickness of about 0.1 to 5.0 microns.

6. In vivo-soluble composite particles according to claim 1 in which said calcium phosphate compound is hydroxyapatite having a Ca/P ratio of about 1.65 to 1.67.

7. In vivo-soluble composite particles according to claim 1 in which an average particle size of calcium phosphate compound particles penetrated into the polymeric particles is less than about one fifth of an average particle size of the polymeric particles.

8. In vivo-soluble composite particles according to claim 1 in which an average particle size of calcium phosphate compound particles penetrated into the polymeric particles is less than about one tenth of an average particle size of the polymeric particles.

* * * * *